United States Patent [19]

Podszun

[11] Patent Number: 4,617,327

[45] Date of Patent: Oct. 14, 1986

[54] INORGANIC-ORGANIC FILLERS FOR POLYMERIZABLE COMPOSITIONS

[75] Inventor: Wolfgang Podszun, Cologne, Fed. Rep. of Germany

[73] Assignee: Bayer Aktiengesellschaft, Leverkusen, Fed. Rep. of Germany

[21] Appl. No.: 786,256

[22] Filed: Oct. 10, 1985

Related U.S. Application Data

[63] Continuation of Ser. No. 671,373, Nov. 14, 1984, abandoned.

[30] Foreign Application Priority Data

Nov. 19, 1983 [DE] Fed. Rep. of Germany ....... 3341888

[51] Int. Cl.$^4$ .......................... C08F 2/44; C08K 9/10; C08K 9/06; A61K 6/08
[52] U.S. Cl. .................................. 523/116; 523/203; 523/206; 524/806; 524/858
[58] Field of Search ...................... 523/116, 203, 206; 524/806, 858

[56] References Cited

U.S. PATENT DOCUMENTS

| | | | |
|---|---|---|---|
| 3,258,444 | 6/1966 | Santelli | 524/858 |
| 3,471,439 | 10/1969 | Bixler et al. | 523/203 |
| 3,503,128 | 3/1970 | Boyd et al. | 523/203 |
| 3,505,279 | 4/1970 | Preston et al. | 523/203 |
| 3,578,629 | 5/1971 | McManimie | 523/203 |
| 3,897,586 | 7/1975 | Coker | 428/403 |
| 4,028,325 | 6/1977 | King et al. | 523/115 |
| 4,302,376 | 11/1981 | Walkowiak et al. | 523/117 |
| 4,308,190 | 12/1981 | Walkowiak et al. | 523/309 |
| 4,368,235 | 1/1983 | Vaughn | 524/858 |
| 4,394,465 | 7/1983 | Podszun et al. | 523/220 |
| 4,412,015 | 10/1983 | Lustgarten et al. | 523/116 |
| 4,421,660 | 12/1983 | Solc | 524/785 |
| 4,427,799 | 1/1984 | Orlowski et al. | 523/220 |
| 4,442,240 | 4/1984 | Suh | 523/203 |

FOREIGN PATENT DOCUMENTS

| | | | |
|---|---|---|---|
| 1937871 | 1/1970 | Fed. Rep. of Germany . | |
| 2405578 | 8/1975 | Fed. Rep. of Germany . | |
| 84/00375 | 2/1984 | PCT Int'l Appl. | 523/203 |
| 1358350 | 7/1974 | United Kingdom | 523/203 |

OTHER PUBLICATIONS

Research Disclosure, No. 162, Oct. 1977, (GB) Seite 80, Spalte No. 16269, "New Dental Materials".

*Primary Examiner*—Herbert J. Lilling
*Attorney, Agent, or Firm*—Sprung Horn Kramer & Woods

[57] ABSTRACT

A filler for a polymerizable composition comprising an inorganic core of particles with a particle size of 10 to 500 nm, a first shell of vinylsilane and a second shell of a (meth)acrylate polymer. The filler is then used to prepare dental moldings of acrylates in conventional manner. The moldings are very hard and abrasion resistant.

12 Claims, No Drawings

INORGANIC-ORGANIC FILLERS FOR POLYMERIZABLE COMPOSITIONS

This is a continuation of application Ser. No. 671,373, filed Nov. 14, 1984, and now abandoned.

The invention relates to a filler for polymerizable compositions, in particular dental materials, consisting of an inorganic core, a first shell of a polymerized vinylsilane and a second shell of acrylate or methacrylate polymers.

Polymer systems filled with inorganic fillers are widely used in dental materials. Thus, hardenable mixtures of (meth)acrylic acid esters, as polymerizable binders, and fine-particled inorganic fillers are in general used as dental filling materials based on plastics.

These fillers can be classified according to their particle size as "macrofillers", with a particle size of about 1 $\mu$m to about 50 $\mu$m (preferably about 30 $\mu$m) and as "microfillers" with a particle size of about 5–500 nm. Dental materials based on "macrofillers" are described, for example, in U.S. Pat. No. 3,066,112, U.S. Pat. No. 3,926,906, DE-OS (German Published Specification) No. 2,357,324 and DE-OS (German Published Specification) No. 2,419,887.

DE-OS (German Published Specification) No. 2,403,211 and DE-OS (German Published Specification) No. 2,462,271 disclose materials for dental purposes which contain, as an inorganic filler, exclusively microfine silicon dioxide with a particle size of 5 to 700 nm. Compared with the "macrofiller products", the "microfiller products" are significantly easier to polish, but in general have a lower degree of filling, which has an adverse effect on some physical properties, such as polymerization shrinkage, coefficient of thermal expansion and absorption of water. Moreover, formulations of "microfillers" and polymerizable binders have poor processing properties because of their high tackiness. Various routes have been taken to counteract the difficulties of incorporating "microfillers" into monomeric binders. Thus, it is possible to replace all or some of the "microfiller particles" by "microfiller"-containing prepolymers in chip form. The incorporation of "microfiller particles" into bead polymers is a further improvement (European Patent A No. 001,190). The use of filler-containing prepolymers in chip or bead form leads to "microfiller products" with a filler content of about 50% by weight as the upper limit. Higher degrees of filling can be achieved by agglomerating the "microfillers" before use and grinding the agglomerates to granules, but losses must be tolerated in respect of homogeneity and ease of polishing of the dental material (PCT/EP No. 80/00135).

Coating of "macrofillers" with organic polymers for the purpose of increasing the ease of incorporation into dental materials is a known method. Thus, DE-OS (German Published Specification) No. 1,937,871 describes a finely divided silicon dioxide or silicate filler coated with a vinylsilane as a base coat and with an acrylic polymer. European Patent A No. 0,047,971 likewise discloses mineral particles and coated with plastic. Glass granules coated with synthetic polymers are known as fillers for dental filling compositions from Japanese Patent A No. 74-042,905.

However, these known coating processes cannot be applied in the manner described to "microfillers", since "microfillers" tend to form agglomerates during aftertreatment because of their extremely low particle size and high specific surface area, which means that the advantageous properties of the "microfillers" are lost.

The object of the present invention is to provide a filler based on "microfillers", for dental materials, which allows a high degree of filling and leads to materials which can easily be polished and have high mechanical strengths.

The invention relates to a filler with an inorganic core, a first shell of polymerized vinylsilane and a second shell of (meth)acrylate polymers, which is characterized in that the inorganic core consists of highly disperse particles with a particle size of 10 to 500 nm.

The filler according to the invention can be obtained by dispersing a highly disperse filler in an organic solvent, silanizing the filler in a first step with a mixture of vinylsilane, water and acid and encasing the product with (meth)acrylate polymers in a second step by polymerization.

Suitable highly disperse fillers are all the conventional inorganic fillers with particle sizes of 10–500 nm, in particular 10–100 nm, preferably those based on aluminum oxide, silicon dioxide and silicates. Silicon dioxide and aluminum dioxide obtained by flame hydrolysis and having a particle size of 10 to 40 nm and a BET surface area of 30 to 300 $m^2/g$, preferably 40 to 200 $m^2/g$, are particularly preferred.

The vinylsilanes which are known per se from the abovementioned printed publications, such as, for example, vinyltriethoxysilane, vinyltrimethoxysilane, $\gamma$-methacryloxypropyltrimethoxysilane, $\gamma$-methacryloxypropyl-tri(2-methoxy)-silane or vinyltriacetoxysilane can be used, for example, for the first shell of vinylsilane. $\gamma$-Methacryloxypropyltrimethoxysilane is preferably used. The amount of silane compound is preferably 2–40% by weight, particularly preferably 5–25% by weight, based on the highly disperse filler.

To prepare the fillers according to the invention, it is necessary to maintain defined silanization conditions. The silane compound is converted into an activated form in a first reaction stage by reaction with water. In this preliminary reaction, the less reactive alkoxy or acetoxy groups of the silane compound are probably hydrolyzed to the more reactive silanol groups. This reactive mixture is not stable on storage and must be freshly prepared each time before the silanization reaction. The reaction time required for the silane-water preliminary reaction depends on the reaction temperature and is as a rule in the range from 15 minutes to 2 hours at room temperature. Particularly good results are achieved if the water and silane compound are used in approximately the same amounts by weight. The most advantageous reactivity of the silane compound occurs at the time at which the initially two-phase water/silane mixture has just become a single-phase system. Either mineral acids or organic acids can be used as the catalyst. Acrylic acid and methacrylic acids, for example, are particularly suitable. The acid is preferably used in amounts of 0.1 to 5% by weight, particularly preferably 0.5 to 2% by weight, based on the silane compound.

The silanization is preferably carried out in the presence of an inert organic solvent, such as, for example, acetone, ethyl acetate, chloroform or methylene chloride. The highly disperse filler is preferably dispersed in the organic solvent in a concentration of 5–40% by weight, particularly preferably 15–25% by weight, with the aid of a high-speed stirrer, and the prepared active silane/water mixture is added. The silanization reaction can be carried out between 0° and 100° C., for example at room temperature, but advantageously at elevated temperature, for example at the boiling point of the solvent.

The reaction time is in general a few hours. During the silanization, the viscosity of the dispersion decreases, so that the end of the reaction can be determined in a simple manner by continuous measurement of the viscosity.

To build up the second shell, (meth)acrylate monomers and a polymerization initiator are added to the dispersion of the silanized filler in an inert organic solvent and the polymerization reaction is started. The monomers can be added all at once in one portion at the start of the reaction. However, it is more advantageous to meter the monomers and the polymerization initiator into the reaction mixture in portions over a longer period of time.

Suitable (meth)acrylate monomers are both monofunctional (meth)acrylates and di- and tri-(meth)acrylates. In a particular embodiment of the present invention, at least a proportion of di- or tri-(meth)acrylates is added, so that the second shell is crosslinked.

Examples of mono-(meth)acrylates which can be used are: methyl(meth)acrylate, ethyl(meth)acrylate, butyl(meth)acrylate, lauryl(meth)acrylate, cyclohexyl(meth)acrylate and dihydrodicyclopentadienyl(meth)acrylate.

Examples of di(meth)acrylates which may be mentioned are: ethylene glycol di(meth)acrylate, diethylene glycol di(meth)acrylate, triethylene glycol di(meth)acrylate, neopentylglycol di(meth)acrylate, 1,12-dodecane di(meth)acrylate, and furthermore derivatives of bisphenol A, such as 2,2-bis-4(2-hydroxy-3-methacryloyloxypropyl)phenyl-propane (bis GMA) and urethane di(meth)acrylates, such as are described, for example, in U.S. Pat. Nos. 3,425,988, 3,709,866 and 3,629,187.

Examples of possible tri(meth)acrylates are: glycerol tri(meth)acrylate, trimethylolpropane tri(meth)acrylate and pentaerythritol tri(meth)acrylate.

The term (meth)acrylate means both methacrylate and acrylate. The methacrylates are preferably used for the preparation of the fillers according to the invention. Besides the (meth)acrylates, it is also possible to use up to 20% by weight, based on the sum of the (meth)acrylate monomers, of other vinyl or vinylidene monomers, such as, for example, styrene, α-methylstyrene, acrylonitrile or vinylacetate. The (meth)acrylate monomers are preferably used in amounts of 3–100% by weight, particularly preferably 10–50% by weight, based on the highly disperse filler. The choice of the (meth)acrylate monomers used is made in view of the desired intended use of the filler according to the invention. It is thus advantageous, for example, for use in teeth made of polymethylmethacrylate plastic, to copolymerize at least a proportion of methyl methacrylate in the second shell in order to achieve a good tolerance.

The customary soluble agents which form free radicals can be used to initiate the polymerization; examples which may be mentioned are: peroxide and azo compounds, such as dibenzoyl peroxide, dilauroyl peroxide, cyclohexyl percarbonate and azoisobutyrodinitrile. Mixtures of polymerization initiators with different decomposition temperatures are also particularly suitable. The polymerization is started by heating to the decomposition temperature of the polymerization initiator. The polymerization can be carried out under increased pressure, for example under a nitrogen pressure of 2 to 6 bar. The mixture is preferably stirred with a high-speed stirrer during the polymerization.

The filler according to the invention can be obtained from the polymerized dispersion by evaporating off the solvent. It is also possible to flocculate out the polymer, for example by addition of methanol, and to filter it off. It is particularly advantageous to use a spray-drying process, in which a fine-particled, free-flowing product is obtained.

The filler according to the invention, in particular the filler isolated by spray-drying, can advantageously be used in polymerizable compositions, in particular in the preparation of dental plastics. The filler is easily wettable, outstandingly dispersible and can be incorporated with high degrees of filling into monomeric binders. Shaped articles, for example false teeth or dental fillings, containing the filler according to the invention, are distinguished by a high mechanical strength and, in particular, a high abrasion resistance.

The polymerizable compositions according to the invention contain 20 to 65% by weight, preferably 20 to 50% by weight and in particular 25 to 45% by weight, of a polymerizable monomer, 10 to 75% by weight, preferably 20 to 75% by weight and in particular 30 to 70% by weight, of the filler according to the invention and, if appropriate, further inorganic or organic fillers, polymerization initiators, inhibitors, dyestuffs and other additives, which are known per se. If large amounts of polyfunctional monomers (crosslinking agents) are used and for certain intended uses it may be advantageous to add plasticizers to the polymerizable compositions according to the invention in order to reduce the brittleness. High molecular weight plasticizers which are known per se, in particular those based on polyurethanes, polycarbonates, polyesters and polyethers, are above all particularly suitable. Polyesters and polyester-carbonates, which are described in German Patent Application P No. 33 16 851.2 are preferred. Examples of possible polymerizable monomers and polymerization initiators are the compounds mentioned above in connection with the preparation of the second shell of the filler. The polymerizable compositions are particularly suitable for the preparation of shaped dental articles, and also as bone cements and for other orthopaedic applications.

EXAMPLE 1

19.8 kg of methylene chloride and 3.8 kg of highly disperse silicon dioxide (particle size about 20 nm, BET surface area 50 m$^2$/g) are weighed into a 40 liter stirred autoclave which can be heated, and the stirrer speed is adjusted to 400 rpm. 760 g of γ-methacryloxypropyl-trimethoxysilane, 980 g of deionized water and 10.4 g of methacrylic acid are mixed in a separate glass vessel. As soon as the mixture is a single-phase system (after about 40 minutes at room temperature) it is added in one portion to the stirrer autoclave. The temperature in the stirred autoclave is kept at 40° C. for 20 hours, and 0.38 kg of methyl methacrylate, 0.38 kg of isobutyl methacrylate, 8 g of ethylene dimethacrylate and 20 g of azoisobutyrodinitrile are then added, a pressure of 5 bar of N$_2$ is applied and the temperature is kept at 70° C. for 3 hours and then at 80° C. for a further 3 hours. After cooling, the dispersion is diluted with 10 kg of methylene chloride and subjected to a spray-drying process. 5.1 kg of fine-particled filler are obtained.

EXAMPLE 2

Example 1 is repeated, the following amounts being used: 19.8 kg of methylene chloride, 3.8 kg of highly disperse silicon dioxide (particle size about 20 nm, BET surface area 50 m²/g), 456 g of γ-methacryloxypropyl-trimethoxysilane, 588 g of deionized water, 6 g of methacrylic acid, 550 g of methyl methacrylate, 11 g of ethylene dimethacrylate and 20 g of azoisobutyrodinitrile. 4.8 kg of fine-particled filler are obtained.

EXAMPLE 3

65 g of bisphenol A diglycidyl dimethacrylate, 35 g of triethylene glycol dimethacrylate, 318 g of the fine-particled filler of Example 1, 2 g of dibenzoyl peroxide and small amounts (<0.1 g) of customary pigments are kneaded to a paste in a kneader. To produce teeth, this paste is pressed into molds and hardened at 130° C. in the course of 6 minutes. The resulting teeth are distinguished by being very hard and having a high abrasion resistance.

EXAMPLE 4

75 g of methyl methacrylate, 20 g of ethylene dimethacrylate, 5 g of a polyester containing polycarbonate groups (Example 3 of DE-OS (German Published Specification) No. 2,732,718), 30 g of polymethyl-methacrylate bead polymer (d$_{50}$: 45 μm, [η] in CHCl$_3$: 1.8 dl/g) and 220 g of fine-particled filler from Example 2 are kneaded to a paste-like composition in a kneader. This composition is activated with 2 g of dibenzoyl peroxide and colored the color of teeth with the customary pigments. After a maturing time of 30 minutes, the composition is pressed into teeth molds and hardened at 120° C. for 8 minutes. The resulting teeth are distinguished by being very hard and having a high abrasion resistance.

It will be appreciated that the instant specification and examples are set forth by way of illustration and not limitation, and that various modifications and changes may be made without departing from the spirit and scope of the present invention.

I claim:

1. A filler for a polymerizable composition comprising an inorganic core of particles with a particle size of 10 to 500 nm, a first shell of vinylsilane and a second shell of a (meth)acrylate polymer.

2. A filler according to claim 1, wherein the first shell is present in about 2–40% by weight of the inorganic core.

3. A filler according to claim 1, wherein the second shell is present in about 3–100% by weight of the inorganic core.

4. A filler according to claim 1, wherein the inorganic core comprises silicon dioxide, a silicate and/or aluminum oxide.

5. A filler according to claim 4, wherein the inorganic core comprises silicon dioxide, and/or aluminum oxide with a particle size of about 10 to 40 nm which has been obtained by flame hydrolysis.

6. A filler according to claim 1, wherein the BET surface area of the inorganic core is about 30 to 300 m²/g.

7. A filler according to claim 1, wherein the second shell is crosslinked.

8. A filler according to claim 1, wherein the first shell is present in about 5 to 25% and the second shell in 10 to 50% by weight of the inorganic core, the core having a BET surface area of about 40 to 200 m²/g.

9. A composition by weight comprising about 20 to 65 parts of a polymerizable monomer and about 10 to 75 parts of a filler according to claim 1.

10. An article molded from a composition according to claim 9.

11. A dental bridge, tooth or filling molded from a composition according to claim 9.

12. A process for preparing a filler according to claim 1, comprising dispersing inorganic particles of 10 to 500 nm in an organic solvent, silanizing said particles with a reactive mixture of a vinylsilane and water to form the first shell about the particles, and polymerizing a meth(acrylate) monomer about the first shell to form the second shell.

* * * * *

UNITED STATES PATENT AND TRADEMARK OFFICE
CERTIFICATE OF CORRECTION

PATENT NO. : 4,617,327
DATED : October 14, 1986
INVENTOR(S) : Wolfgang Podszun

It is certified that error appears in the above-identified patent and that said Letters Patent are hereby corrected as shown below:

Col. 1, lines 45, 60 and 65     Delete "A No." and substitute --No. A --

Col. 1, line 61                 After "particles" delete "and"

Col. 4, line 40                 Delete "P No." and substitute --No. P --

Col. 6, line 24                 Delete "claim 1" and substitute --claim 5--

Signed and Sealed this

Twentieth Day of January, 1987

Attest:

DONALD J. QUIGG

Attesting Officer     Commissioner of Patents and Trademarks